United States Patent
Moaddeb

(10) Patent No.: US 6,671,561 B1
(45) Date of Patent: Dec. 30, 2003

(54) CATHETER WITH ELECTRODE HAVING HYDROGEL LAYER

(75) Inventor: Shahram Moaddeb, Woodland Hills, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/561,716

(22) Filed: May 1, 2000

(51) Int. Cl.⁷ ................................................. A61N 1/05
(52) U.S. Cl. ...................................................... 607/120
(58) Field of Search ...................... 607/119–122, 115, 607/116, 117, 118

(56) References Cited

U.S. PATENT DOCUMENTS

| | | | |
|---|---|---|---|
| 3,709,810 A | 1/1973 | Grubb et al. | 204/195 R |
| 4,440,178 A | 4/1984 | Bussard et al. | 128/784 |
| 4,603,704 A | 8/1986 | Mund et al. | |
| 4,762,136 A | 8/1988 | Baker, Jr. | 128/786 |
| 4,853,091 A | 8/1989 | Mund et al. | 204/1 T |
| 4,858,623 A | 8/1989 | Bradshaw et al. | 128/785 |
| 4,913,164 A | 4/1990 | Greene et al. | 128/785 |
| 4,922,927 A | 5/1990 | Fine et al. | 128/786 |

(List continued on next page.)

OTHER PUBLICATIONS

Biotronik, pages from web site, www.biotronik.com, 4 pages, available at least as early as Sep. 28, 1999.
Moaddeb, S. et al., "In Vivo Performance of a New Micro/Macro–Porous, Titanium Nitride Coated Electrode", Siemens Pacesetter, Inc., Sylmar, California, U.S.A., 1 page.
Moaddeb, S. et al., "In Vivo Results of Comparisons of Sub–Acute Performance of Titanium Nitride, Steroid Platinized, and Activated Carbon Electrodes", Siemens Pacesetter, Inc., Sylmar, California, U.S.A., 1 page.

*Primary Examiner*—Scott M. Getzow
(74) *Attorney, Agent, or Firm*—Christie, Parker & Hale, LLP

(57) ABSTRACT

A catheter having an improved electrode that minimizes irritation to the heart tissue and counters the occurrence of foreign body reactions is provided. The catheter comprises an elongated, flexible catheter body having proximal and distal ends and at least one lumen extending therethrough. At least one electrode, such as a tip electrode or ring electrode, is mounted on the distal end of the catheter body, wherein the electrode comprises a base material having an outer surface and a hydrogel layer applied over at least a portion of the outer surface of the base material. Preferably a drug or other therapeutic agent is incorporated into the hydrogel layer.

37 Claims, 4 Drawing Sheets

U.S. PATENT DOCUMENTS

| | | | |
|---|---|---|---|
| 4,976,703 A | 12/1990 | Franetzki et al. | 604/247 |
| 5,007,424 A | 4/1991 | Ahsbahs et al. | 128/635 |
| 5,250,168 A | 10/1993 | Tsukada et al. | 204/416 |
| 5,282,845 A | 2/1994 | Bush et al. | 607/128 |
| 5,296,122 A | 3/1994 | Katsube et al. | 204/298.04 |
| 5,318,572 A | 6/1994 | Helland et al. | 607/121 |
| 5,352,352 A | 10/1994 | Tsukada et al. | 204/415 |
| 5,431,681 A * | 7/1995 | Helland | |
| 5,439,485 A | 8/1995 | Mar et al. | 607/119 |
| 5,447,533 A | 9/1995 | Vachon et al. | 607/120 |
| 5,476,496 A | 12/1995 | Strandberg et al. | 607/122 |
| 5,488,768 A | 2/1996 | Mar | 29/860 |
| 5,534,022 A | 7/1996 | Hoffmann et al. | 607/122 |
| 5,542,173 A | 8/1996 | Mar et al. | 29/825 |
| 5,551,427 A | 9/1996 | Altman | 128/642 |
| 5,571,158 A | 11/1996 | Bolz et al. | 607/121 |
| 5,579,583 A | 12/1996 | Mehregany et al. | 30/342 |
| 5,609,611 A | 3/1997 | Bolz et al. | 607/13 |
| 5,614,246 A | 3/1997 | Mund et al. | 427/2.24 |
| 5,632,770 A | 5/1997 | Schaldach | 607/122 |
| 5,645,580 A | 7/1997 | Moaddeb et al. | 607/122 |
| 5,658,282 A | 8/1997 | Daw et al. | 606/49 |
| 5,716,392 A | 2/1998 | Bourgeois et al. | 607/132 |
| 5,718,726 A | 2/1998 | Amon et al. | 623/2 |
| 5,720,775 A | 2/1998 | Larnard | 607/122 |
| 5,728,089 A | 3/1998 | Lal et al. | 606/1 |
| 5,733,323 A | 3/1998 | Buck et al. | 607/122 |
| 5,746,616 A | 5/1998 | Mar | 439/245 |
| 5,782,879 A | 7/1998 | Rosborough et al. | 607/6 |
| 5,824,030 A | 10/1998 | Yang et al. | 607/122 |
| 5,833,715 A | 11/1998 | Vachon et al. | 607/120 |
| 5,861,023 A | 1/1999 | Vachon | 607/121 |
| 5,882,346 A * | 3/1999 | Pomeranz et al. | |
| 5,891,048 A | 4/1999 | Nigam et al. | 600/521 |
| 5,891,169 A | 4/1999 | Boheim et al. | 607/4 |
| 5,902,329 A * | 5/1999 | Hoffmann et al. | |
| 5,908,447 A | 6/1999 | Schroeppel et al. | 607/126 |
| 5,925,069 A | 7/1999 | Graves et al. | 607/36 |
| 5,948,014 A | 9/1999 | Valikai | 607/123 |
| 5,957,996 A | 9/1999 | Shiraishi | 708/201 |
| 5,997,532 A * | 12/1999 | McLaughlin et al. | |
| 6,360,129 B1 * | 3/2002 | Ley et al. | |

* cited by examiner

CATHETER WITH ELECTRODE HAVING HYDROGEL LAYER

FIELD OF THE INVENTION

The present invention is directed to a catheter having an enhanced ablation electrode with having a hydrogel layer.

BACKGROUND OF THE INVENTION

Electrode catheters have been in common use in medical practice for many years. They are used to stimulate and map electrical activity in the heart and to ablate sites of aberrant electrical activity.

In use, the electrode catheter is inserted into a major vein or artery, e.g., femoral artery, and then guided into the chamber of the heart which is of concern. Within the heart, the ability to control the exact position and orientation of the catheter tip is critical and largely determines how useful the catheter is.

A typical ablation procedure involves the insertion of a catheter having a tip electrode at its distal end into a heart chamber. A reference electrode is provided, generally taped to the skin of the patient. RF (radio frequency) current is applied to the tip electrode, and current flows through the media that surrounds it, i.e., blood and tissue, toward the reference electrode. The distribution of current depends on the amount of electrode surface in contact with the tissue as compared to blood, which has a higher conductivity than the tissue. Heating of the tissue occurs due to its electrical resistance. The tissue is heated sufficiently to cause cellular destruction in the cardiac tissue resulting in formation of a lesion within the cardiac tissue which is electrically non-conductive. During this process, heating of the electrode also occurs as a result of conduction from the heated tissue to the electrode itself. If the electrode temperature becomes sufficiently high, possibly above 60° C., a thin transparent coating of dehydrated blood protein can form on the surface of the electrode. If the temperature continues to rise, this dehydrated layer can become progressively thicker resulting in blood coagulation on the electrode surface. Additionally, the irritation of the endocardial tissue, as well as the patient's natural foreign body reaction to the presence of the electrode, results in the initiation of the inflammatory response and subsequent fibrous capsule development. The fibrous capsule increases in thickness in an attempt by the body to wall-off the foreign material.

Thus, a need exists for an improved catheter design that minimizes irritation and counters, delays or suppresses the occurrence of the inflammatory response and therefore the growth of the fibrous capsule.

SUMMARY OF THE INVENTION

The present invention is directed to a catheter having an improved electrode that minimizes irritation to the heart tissue and counters the occurrence of foreign body reactions. In one embodiment, the invention is directed to a catheter comprising an elongated, flexible catheter body having proximal and distal ends and at least one lumen extending therethrough. At least one electrode, such as a tip electrode or ring electrode, is mounted on the distal end of the catheter body, wherein the electrode comprises a base material having an outer surface and a hydrogel layer applied over at least a portion of the outer surface of the base material. Preferably a drug or other therapeutic agent is incorporated into the hydrogel layer.

In another embodiment, the invention is directed to an ablation system comprising a catheter as described above and a source of radio frequency energy electrically connected to the electrode.

In another embodiment, the invention is directed to a method for ablating tissue in a patient. The method comprises introducing the distal end of a catheter as described above into the patient so that the electrode is in contact with the tissue to be ablated and applying energy to electrode, thereby creating a lesion in the tissue.

DESCRIPTION OF THE DRAWINGS

These and other features and advantages of the present invention will be better understood by reference to the following detailed description when considered in conjunction with the accompanying drawings wherein.

DETAILED DESCRIPTION

Figure 1:
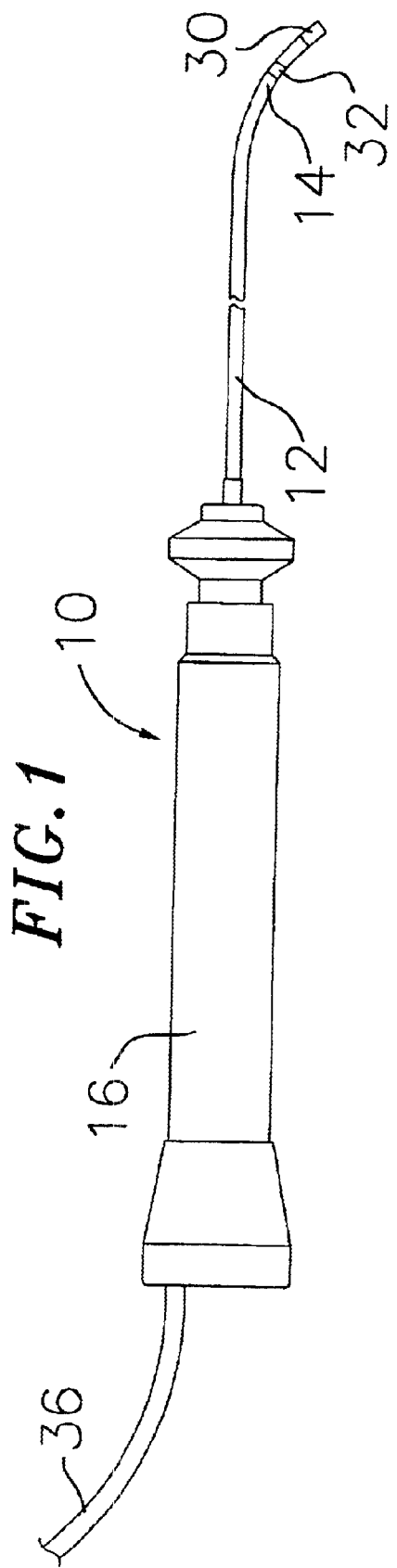
FIG. 1 is a side view of an embodiment of the catheter of the invention.
Figure 2:
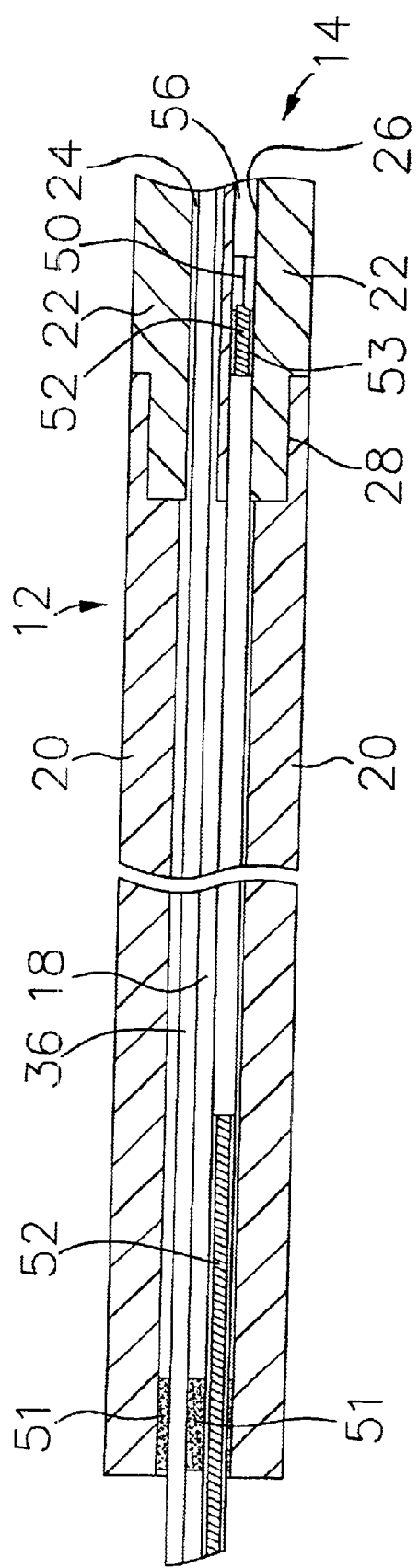
FIG. 2 is a side cross-sectional view of a catheter body according to the invention, including the junction between the catheter body and tip section.
Figure 3:
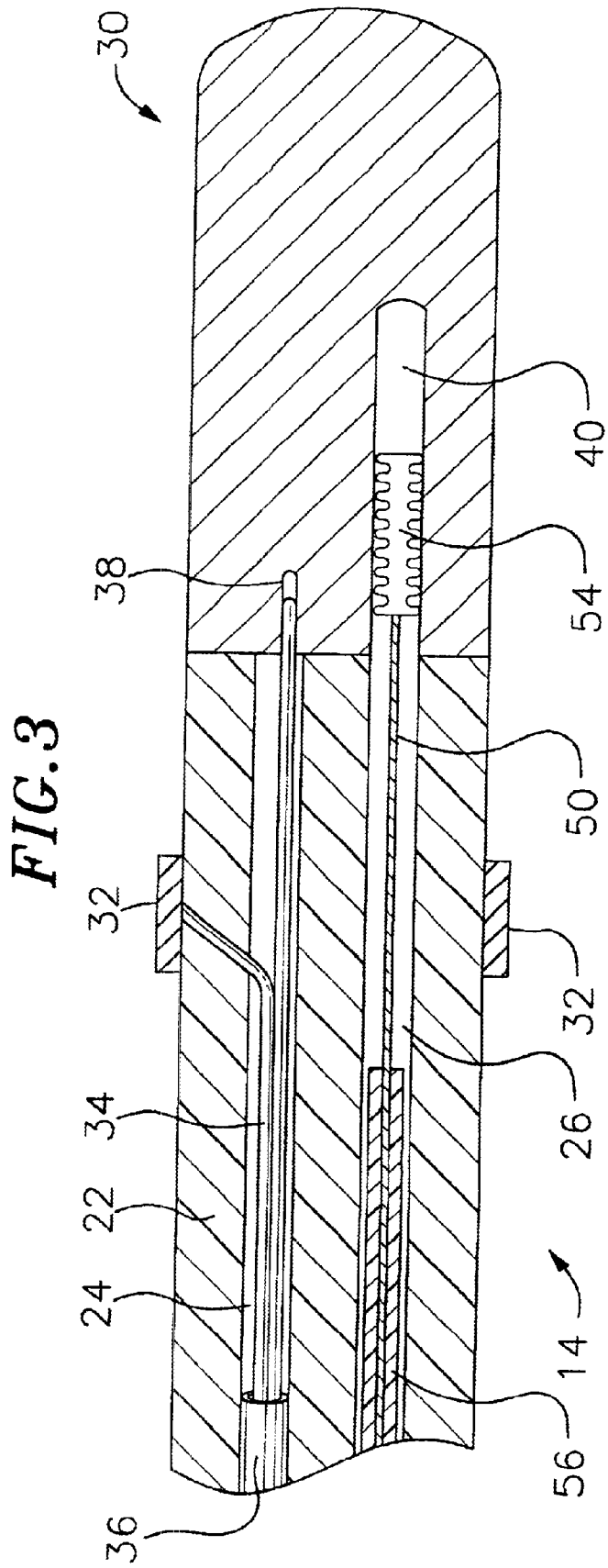
FIG. 3 is a side cross-sectional view of a catheter tip section in accordance with the invention.

In a particularly preferred embodiment of the invention, there is provided a steerable catheter having a hydrogel-coated electrode. As shown in FIGS. 1 to 3, the catheter 10 comprises an elongated catheter body 12 having proximal and distal ends, a tip section 14 at the distal end of the catheter body 12, and a control handle 16 at the proximal end of the catheter body 12.

With reference to FIG. 2, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A presently preferred construction comprises an outer wall 20 made of a polyurethane or PEBAX. The outer wall 20 comprises an imbedded braided mesh of high-strength steel, stainless steel or the like to increase torsional stiffness of the catheter body 12 so that, when the control handle 16 is rotated, the tip section 14 of the catheter 10 will rotate in a corresponding manner. The outer diameter of the catheter body 12 is not critical, but is preferably no more than about 8 french, more preferably no more than about 7 french, still more preferably no more than about 6 french. Likewise the thickness of the outer wall 20 is not critical, but is thin enough so that the central lumen 18 can accommodate a puller wire, lead wire(s), and any other wires, cables or tubes. If desired, the inner surface of the outer wall 20 can be lined with a stiffening tube (not shown), as described in U.S. Pat. No. 5,897,529, the entire disclosure of which is incorporated herein by reference.

As shown in FIGS. 2 and 3, the tip section 14 comprises a short section of tubing 22 having two lumens 24 and 26, although additional lumens can be provided if desired. The tubing 22 is made of a suitable non-toxic material that is preferably more flexible than the catheter body 12. A presently preferred material for the tubing 22 is braided polyurethane, i.e., polyurethane with an embedded mesh of braided high-strength steel, stainless steel or the like. The outer diameter of the tip section 14, like that of the catheter body 12, is preferably no greater than about 8 french, more preferably no more than about 7 french, still more preferably no more than about 6 french. The number and size of the lumens is not critical and depends on the specific application for which the catheter is to be used.

The useful length of the catheter, i.e., that portion that can be inserted into the body, can vary as desired. Preferably the useful length is at least about 100 cm, and more preferably ranges from about 110 cm to about 120 cm. The length of the tip section 14 is a relatively small portion of the useful length, and preferably ranges from about 3.5 cm to about 10 cm, more preferably from about 5 cm to about 6.5 cm.

A preferred means for attaching the catheter body 12 to the tip section 14 is illustrated in FIG. 2. The proximal end of the tip section 14 comprises an outer circumferential notch 28 that receives the inner surface of the outer wall 20 of the catheter body 12. The tip section 14 and catheter body 12 are attached by adhesive (e.g., polyurethane glue) or the like.

At the distal end of the tip section 14 is a tip electrode 30. The tip electrode 30 is attached to the tip section 14 with polyurethane glue or the like, or by any other suitable method known in the art. Preferably the tip electrode 30 has a diameter about the same as the outer diameter of the tubing 22 (e.g., less than or equal to 8 French, preferably less than or equal to 7 French). The tip electrode 30 has a length sufficient for ablating a lesion in heart tissue, preferably at least about 3 mm, more preferably from about 3 mm to about 6 mm, still more preferably from about 3.8 mm to about 4.5 mm.

The tip electrode 30 is made of a base material having an outer surface and comprising any suitable electrically-conductive material, such as platinum, gold, iridium, titanium, tantalum, stainless steel and alloys thereof. In a particularly preferred embodiment, the electrode comprises a platinum-iridium alloy (having 90% platinum by weight and 10% iridium by weight). Alternatively, the base material can comprise a non-metallic but electrically-conductive material, such as ceramic or electrically-conductive plastic. As would be recognized by one skilled in the art, other electrically-conductive materials can also be used for the tip electrode.

The tip electrode 30 is provided with a hydrogel layer over at least a portion, and preferably over all, of the outer surface of the base material. The hydrogel layer can be made from a polymeric material or a protein. Preferred polymeric materials include polyglycolic acid, polylactic acid, copolymers of lactic/glycolic acids, polyesters, polyorthoesters, polyanhydrides, and polyaminoacids. Particularly preferred polymeric materials include polyvinylpyroolidone and SLIP-COAT® (a hybrid polymer system based on polyvinylpyrrolidone and cellulose esters formulated in organic solvent solutions, commercially available from STS Biopolymers, Inc., Henrietta, N.Y.). The polymeric material can be applied to the tip electrode to form the hydrogel layer by any suitable technique, such as by a dip process or a spray process, followed by drying at 40° to 100° C. Any other application techniques known to those skilled in the art can be used. Preferably techniques include where the coating can be applied at lower temperatures, preferably room temperature, such as UV curing coating, because such techniques will not impact the drug or other agent included the hydrogel. Preferred proteins include albumin, collagen and gelatin. Preferably the hydrogel layer has a thickness ranging from about 10 $\mu$m to about 300 $\mu$m, more preferably from about 50 $\mu$m to about 200 $\mu$m.

The hydrogel layer creates a more lubricous surface on the tip electrode, allowing the electrode to be maneuvered more easily and safely into position with less patient trauma. Additionally, the hydrogel layer creates a surface on the tip electrode to which coagulate will not stick, which is particularly beneficial for ablation procedures.

Additionally, the hydrogel layer can be combined with drugs or other therapeutic agents to allow delivery of the drugs or agents by diffusion, co-dissolution and/or resorption. Suitable agents for impregnation into the hydrogel layer include, for example, anti-inflammatory agents, anti-thrombogenic agents, antibiotics, and antimicrobials. Examples of suitable coating materials incorporating are those sold under the name STS HEPARIN (such as heparin-benzalkonium chloride in isopropanol and heparin-tridodecylmethylammonium chloride in other solvents, commercially available from STS Biopolymers, Inc.).

In a particularly preferred embodiment, the hydrogel layer is provided with an anti-inflammatory agent. During an ablation procedure, the irritation of the endocardial tissue, as well as the patient's natural foreign body reaction to the presence of the electrode, results in the initiation of the inflammatory response and subsequent fibrous capsule development. The fibrous capsule increases in thickness in an attempt by the body to wall-off the foreign material. In order to counter, delay or suppress the occurrence of the inflammatory response and therefore the growth of the fibrous capsule, an anti-inflammatory agent is provided in the hydrogel layer. Typically, the drug is intended to counter thrombus formation, fibrosis, inflammation or arrhythmias, or any combination thereof. A particularly preferred anti-inflammatory agent for the minimization of inflammation resultant from foreign body reactions to the surrounding tissue is dexamethasone sodium phosphate.

If desired, the tip electrode 30 can also be provided with a porous layer that has good electrical conductivity over at least a portion, and preferably over all, of the outer surface of the base material. In other words, the porous layer is provided between the base material and the hydrogel layer.

The porous layer is made of metal nitride, metal oxide, metal carbide, metal carbonitride, carbon, carboxy nitride, or a combination thereof. The porous layer should also have good thermal conductivity, preferably equal to or exceeding that of platinum. The metal is preferably selected from titanium, iridium, platinum, vanadium, zirconium, niobium, ruthenium, molybdenum, hafnium, tantalum cerium, chromium, yttrium, aluminum, nickel, and tungsten. Particularly preferred materials for the porous layer include titanium nitride, iridium oxide, and carbon. The porous layer preferably has a thickness ranging from about 0.1 micron to about 100 microns, more preferably from about 1 micron to about 50 microns, still more preferably from about 5 microns to about 30 microns.

The porous layer can be applied by any suitable technique, including, but not limited to, sputtering, ion implantation, ion plating, vacuum coating, and chemical vapor deposition. For example, a porous layer of titanium nitride can be applied by a reactive sputtering technique where the tip electrode base material is placed in a sputter chamber. Ion (such as argon) is accelerated toward a titanium target in the presence of nitrogen gas. The high speed impact of ion with the titanium target results in dislodging of atoms from the surface of the titanium target followed by reaction with nitrogen gas to form titanium nitride. During the coating process, the pressure of the nitrogen gas is reduced to create a porous structure.

Figure 4:
FIG. 4 is a photograph showing a hydrogel layer applied on a porous layer on a tip electrode.

The porous layer increases the surface area of the tip electrode by at least a factor of fifty. Preferably the surface area is increased 50 times to 5000 times, more preferably at least 500 times. FIG. 4 is a photograph showing an enlarged view of a porous layer in accordance with the invention, which demonstrates the resulting increased surface area. The porous layer of FIG. 4 comprises titanium nitride applied by a reactive sputtering technique, as described above.

The increased surface area of the tip electrode enhances the ability of the electrode to dissipate heat during ablation. As a result, a given amount of power (e.g., RF energy) can be applied to the tip electrode for a longer period of time than can be applied to a comparable tip electrode without the porous layer while still avoiding significant coagulation on the electrode. In fact, the cooling ability of a tip electrode having the porous layer and a length of about 4 mm is comparable to the cooling ability of an 8 mm tip electrode not having the porous layer. For most ablation procedures, a 4 mm electrode is preferred over an 8 mm electrode, assuming equivalent cooling ability, because multiple thermocouples are needed to accurately measure the temperature of an 8 mm tip electrode, whereas a single thermocouple is sufficient to accurately measure the temperature of a 4 mm tip electrode.

FIG. 4 is a photograph showing an enlarged view of a hydrogel layer applied over a porous layer in accordance with the invention. The porous layer comprises 4 comprises titanium nitride applied by a reactive sputtering technique, as described above. The hydrogel layer comprises polyvinylpyrrolidone dip-coated onto the electrode and UV-cured.

In the embodiment shown, the tip section 14 further comprises a ring electrode 32 mounted on the tubing 22 proximal to the tip electrode 30. It is understood that the presence and number of ring electrodes 30 may vary as desired. The ring electrode 32 is slid over the tubing 22 and fixed in place by glue or the like. The ring electrode 32 can be made of any suitable material, and is preferably machined from platinum-iridium bar (90% platinum/10% iridium). If desired, the ring electrode 32 can also be covered, in whole or in part, with a hydrogel layer and/or a porous layer as described above. Alternatively, the ring electrode can be covered with the hydrogel layer instead of the tip electrode, although it is presently preferred that the tip electrode be provided with the hydrogel layer.

The tip electrode 30 and ring electrodes 32 are each connected to a separate lead wire 34. The lead wires 34 extend through the first lumen 24 of tip section 14, the central lumen 18 of the catheter body 12, and the control handle 16, and terminate at their proximal end in an input jack (not shown) that is connected to a source of RF energy and optionally plugged into an appropriate monitor (not shown). The portion of the lead wires 34 extending through the central lumen 18 of the catheter body 12, control handle 16 and proximal end of the tip section 14 may be enclosed within a protective sheath 36, which can be made of any suitable material, preferably polyimide. The protective sheath 36 is preferably anchored at its distal end to the proximal end of the tip section 14 by gluing it in the first lumen 24 with polyurethane glue or the like.

The lead wires 34 are attached to the tip electrode 30 and ring electrode 32 by any conventional technique. Connection of a lead wire 34 to the tip electrode 30 is accomplished, for example, by soldering the lead wire 34 into a first blind hole 38 in the tip electrode.

Connection of a lead wire 34 to the ring electrode 32 is preferably accomplished by first making a small hole through the tubing 22. Such a hole can be created, for example, by inserting a needle through the tubing 22 and heating the needle sufficiently to form a permanent hole. A lead wire 34 is then drawn through the hole by using a microhook or the like. The ends of the lead wire 34 are then stripped of any coating and soldered or welded to the underside of the ring electrode 32, which is then slid into position over the hole and fixed in place with polyurethane glue or the like.

One or more temperature sensing means (not shown) are preferably provided for the tip electrode 30 and, if desired, the ring electrodes 32. In a particularly preferred embodiment, a single temperature sensing means is provided in the tip electrode. Any conventional temperature sensing means, e.g., a thermocouple or thermistor, may be used. A preferred temperature sensing means for the tip electrode 30 comprises a thermocouple formed by a wire pair. One wire of the wire pair is a copper wire, e.g., a number 40 copper wire. The other wire of the wire pair is a constantan wire, which gives support and strength to the wire pair. The wires of the wire pair are electrically isolated from each other except at their distal ends where they contact and are twisted together, covered with a short piece of plastic tubing, e.g., polyimide, and covered with epoxy. The plastic tubing is then attached by polyurethane glue or the like in the first blind hole 38 of the tip electrode along with the lead wire 34. The wires extend through the first lumen 24 in the tip section 14. Within the catheter body 12, the wires may extend through the protective sheath 36 with the lead wires 34. The wires then extend out through the control handle 16 and to a connector (not shown) connectable to a temperature monitor (not shown).

Alternatively, the temperature sensing means may be a thermistor. A suitable thermistor for use in the present invention is Model No. AB6N2-GC14KA143E/37C sold by Thermometrics (New Jersey).

Additionally, a mechanism is provided for deflecting the tip section 14. The mechanism comprises a puller wire 50 extending through the catheter body 12. The puller wire 50 is anchored at its proximal end to the control handle 16 and at its distal end to the tip section 14. The puller wire 50 is made of any suitable metal, such as stainless steel or Nitinol, and is preferably coated with Teflon® or the like. The coating imparts lubricity to the puller wire 50. The puller wire 50 preferably has a diameter ranging from about 0.006 to about 0.010 inches.

A compression coil 52 is situated within the catheter body 12 in surrounding relation to the puller wire 50. The compression coil 52 extends from the proximal end of the catheter body 12 to the proximal end of the tip section 14. The compression coil 52 is made of any suitable metal, preferably stainless steel. The compression coil 52 is tightly wound on itself to provide flexibility, i.e., bending, but to resist compression. The inner diameter of the compression coil 52 is preferably slightly larger than the diameter of the puller wire 50. The Teflon® coating on the puller wire 50 allows it to slide freely within the compression coil 52. If desired, particularly if the lead wires 34 are not enclosed by a protective sheath 36, the outer surface of the compression coil 52 can be covered by a flexible, non-conductive sheath, e.g., made of polyimide tubing, to prevent contact between the compression coil 52 and any other wires within the catheter body 12.

The compression coil 52 is anchored at its proximal end to the proximal end of the catheter body 12 by proximal glue joint 51 and at its distal end to the tip section 14 by distal glue joint 53. Both glue joints 51 and 53 preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 20 of the catheter body 12 which is heated sufficiently to form a permanent hole. The glue is then introduced through the hole to the outer surface of the compression coil 52 and wicks around the outer circumference to form a glue joint about the entire circumference of the compression coil 52.

The puller wire 50 extends into the second lumen 26 of the tip section 14. The puller wire 50 is anchored at its distal end to the tip electrode 30 within a second blind hole 40. A preferred method for anchoring the puller wire 50 within the tip electrode 30 is by crimping metal tubing 54 to the distal end of the puller wire 50 and soldering the metal tubing 54 inside the second blind hole 40. Anchoring the puller wire 50 within the tip electrode 30 provides additional support for the tip electrode on the flexible plastic tubing 22, reducing the likelihood that the tip electrode will separate from the tubing. Alternatively, the puller wire 50 can be attached to the side of the tip section 14. Such a design is described in U.S. patent application Ser. No. 08/924,611 (filed Sep. 5, 1997), the disclosure of which is incorporated herein by reference. Within the second lumen 26 of the tip section 14, the puller wire 50 extends through a plastic, preferably Teflon®, sheath 56, which prevents the puller wire 50 from cutting into the wall of the tubing 22 when the tip section is deflected.

Longitudinal movement of the puller wire 50 relative to the catheter body 12, which results in deflection of the tip section 14, is accomplished by suitable manipulation of the control handle 16. A suitable control handle design for use with the present invention is described in U.S. patent application Ser. No. 08/982,113, filed Dec. 1, 1997, the disclosure of which is incorporated herein by reference.

If desired, the catheter can be multidirectional, i.e., having two or more puller wires to enhance the ability to manipulate the tip section in more than one direction or to form two or more different curves. A description of such a design is provided in U.S. patent application Ser. No. 08/924,611 (filed Sep. 5, 1997), U.S. patent application Ser. No. 09/130,359 (filed Aug. 7, 1998), U.S. patent application Ser. No. 09/143,426 (filed Aug. 28, 1998), U.S. patent application Ser. No. 09/205,631 (filed Dec. 3, 1998), and U.S. patent application Ser. No. 09/274,050 (filed Mar. 22, 1999), the disclosures of which is incorporated herein by reference.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
   an elongated, flexible catheter body having proximal and distal ends and at least one lumen extending therethrough; and
   at least one electrode mounted on the distal end of the catheter body, wherein the electrode comprises an electrically-conductive base material having an outer surface with an electrically-conductive porous layer applied over at least a portion of the outer surface of the base material and a hydrogel layer applied over at least a portion of the porous layer.

2. A catheter according to claim 1, further comprising a drug or other therapeutic agent combined with the hydrogel layer.

3. A catheter according to claim 1, further comprising an anti-inflammatory agent combined with the hydrogel layer.

4. A catheter according to claim 1, wherein the electrode is a tip electrode.

5. A catheter according to claim 4, wherein the tip electrode has a length of at least about 3 mm.

6. A catheter according to claim 4, wherein the tip electrode has a length ranging from about 3 mm to about 6 mm.

7. A catheter according to claim 1, further comprising a ring electrode mounted on the distal end of the catheter body, wherein the ring electrode comprises a base material having an outer surface and a hydrogel layer applied over at least a portion of the outer surface of the base material.

8. A catheter according to claim 1, wherein the hydrogel layer has a thickness ranging from about 10 $\mu$m to about 300 $\mu$m.

9. A catheter according to claim 1, wherein the porous layer comprises a material selected from the group consisting of metal nitride, metal oxide, metal carbide, metal carbonitride, carbon, carboxy nitride, and any combination thereof.

10. A catheter according to claim 9, wherein the porous layer comprises titanium nitride or iridium oxide.

11. A catheter according to claim 1, wherein the hydrogel layer comprises a protein.

12. A method according to claim 11, wherein the protein is selected from the group consisting of albumin, collagen and gelatin.

13. A catheter according to claim 1, wherein the porous layer has a thickness ranging from about 1 micron to about 50 microns.

14. A catheter according to claim 1 having a useful length of at least about 100 cm.

15. An ablation system comprising:
   a catheter comprising:
      an elongated, flexible catheter body having proximal and distal ends and at least one lumen extending therethrough, and
      at least one electrode mounted on the distal end of the catheter body, wherein the electrode comprises an electrically-conductive base material having an outer surface with an electrically-conductive porous layer applied over at least a portion of the outer surface of the base material and a hydrogel layer applied over at least a portion of the porous layer; and
   a source of radio frequency energy electrically connected to the electrode.

16. A system according to claim 24, wherein the protein comprises a material selected from the group consisting of albumin, collagen and gelatin.

17. A system according to claim 15, further comprising a drug or other therapeutic agent combined with the hydrogel layer.

18. A system according to claim 15, further comprising an anti-inflammatory agent combined with the hydrogel layer.

19. A system according to claim 15, wherein the electrode is a tip electrode.

20. A system according to claim 15, wherein the hydrogel layer has a thickness ranging from about 10 $\mu$m to about 300 $\mu$m.

21. A system according to claim 15, wherein the porous layer comprises a material selected from the group consisting of metal nitride, metal oxide, metal carbide, metal carbonitride, carbon, carboxy nitride, or a combination thereof.

22. A system according to claim 21, wherein the porous layer comprises titanium nitride or iridium oxide.

23. A catheter according to claim 15, wherein the porous layer is electrically conductive.

24. A catheter according to claim 15, wherein the hydrogel layer comprises a protein.

25. A catheter according to claim 15, wherein the porous layer has a thickness ranging from about 1 micron to about 50 microns.

26. A catheter according to claim 15 having a useful length of at least about 100 cm.

27. A method for ablating tissue in a patient, comprising:

introducing the distal end of a catheter as recited in claim 1 into the patient so that the electrode is in contact with the tissue to be ablated; and applying energy to electrode, thereby creating a lesion in the tissue.

28. A catheter according to claim 27, further comprising a drug or other therapeutic agent combined with the hydrogel layer.

29. A catheter according to claim 27, further comprising an anti-inflammatory agent combined with the hydrogel layer.

30. A catheter according to claim 27, wherein the electrode is a tip electrode.

31. A catheter according to claim 27, wherein the hydrogel layer has a thickness ranging from about 10 $\mu$m to about 300 $\mu$m.

32. A method according to claim 27, wherein the porous layer comprises a material selected from the group consisting of metal nitride, metal oxide, metal carbide, metal carbonitride, carbon, carboxy nitride, or a combination thereof.

33. A method according to claim 32, wherein the porous layer comprises titanium nitride or iridium oxide.

34. A catheter according to claim 27, wherein the hydrogel layer comprises a protein.

35. A system according to claim 34, wherein the protein is selected from the group consisting of albumin, collagen and gelatin.

36. A catheter according to claim 27, wherein the porous layer has a thickness ranging from about 1 micron to about 50 microns.

37. A catheter according to claim 27 having a useful length of at least about 100 cm.

* * * * *

UNITED STATES PATENT AND TRADEMARK OFFICE
CERTIFICATE OF CORRECTION

PATENT NO. : 6,671,561 B1
DATED : December 30, 2003
INVENTOR(S) : Shahram Moaddeb It is certified that error appears in the above-identified patent and that said Letters Patent is hereby corrected as shown below:

Column 8,
Line 35, replace "method" with -- catheter --.

Column 9,
Line 23, replace "catheter" with -- method --.

Column 10,
Lines 1, 4 and 6, replace "catheter" with -- method --;
Line 18, replace "system" with -- method --.

Signed and Sealed this

Twenty-fifth Day of January, 2005

JON W. DUDAS
*Director of the United States Patent and Trademark Office*